(12) United States Patent
Sharma

(10) Patent No.: US 9,700,680 B2
(45) Date of Patent: Jul. 11, 2017

(54) MEDICAL DEVICES AND METHODS FOR CREATING BUBBLES

(71) Applicant: Medtrick Inc, Reno, NV (US)

(72) Inventor: Ajay Sharma, San Jose, CA (US)

(73) Assignee: Medtrick Inc., Reno, NV (US)

( * ) Notice: Subject to any disclaimer, the term of this patent is extended or adjusted under 35 U.S.C. 154(b) by 0 days.

(21) Appl. No.: 15/064,306

(22) Filed: Mar. 8, 2016

(65) Prior Publication Data
US 2016/0287809 A1 Oct. 6, 2016

Related U.S. Application Data

(60) Provisional application No. 62/296,434, filed on Feb. 17, 2016, provisional application No. 62/178,084, filed on Mar. 31, 2015.

(51) Int. Cl.
*A61M 5/00* (2006.01)
*A61M 5/315* (2006.01)
(Continued)

(52) U.S. Cl.
CPC ....... *A61M 5/31596* (2013.01); *A61B 8/0883* (2013.01); *A61B 8/481* (2013.01);
(Continued)

(58) Field of Classification Search
CPC .................................................. A61M 5/31596
See application file for complete search history.

(56) References Cited

U.S. PATENT DOCUMENTS 4,226,236 A * 10/1980 Genese ............... A61M 5/284
604/125
5,423,752 A * 6/1995 Haber ................. A61M 5/19
222/137
(Continued)

OTHER PUBLICATIONS

Attaran et al., "Protocol for Optimal Detection and Exclusion of a Patent Foramen Ovale Using Transthoracic Echocardiography with Agitated Saline Microbubbles", Echocardiography: A Jrnl. of CV Ultrasound & Allied Tech., vol. 23, No. 7, 2006, pp. 616-622.
(Continued)

*Primary Examiner* — Tse Chen
*Assistant Examiner* — Joanne Hoffman
(74) *Attorney, Agent, or Firm* — Knobbe Martens Olson & Bear LLP

(57) ABSTRACT

A dedicated device for detection of vascular shunts can include a first chamber, a second chamber, and a third chamber. The first chamber can be configured to hold liquid, the second chamber to hold gas, and the third chamber can be in communication with the first and second chambers. The third chamber can include small-scale geometric features configured to produce gas bubbles as liquid from the first chamber and gas from the second chamber simultaneously flow into the third chamber. The device can also include a device opening in communication with the third chamber such that a mixture of liquid and gas bubbles can flow out of the device opening. The device can also include a plunger configured to force the liquid and the gas simultaneously from the first and second chambers, through the third chamber to mix with each other and produce bubbles, and further through the device opening.

11 Claims, 16 Drawing Sheets

(51) Int. Cl.
*A61B 8/08* (2006.01)
*A61M 5/19* (2006.01)
*A61M 25/01* (2006.01)
*A61M 16/06* (2006.01)
*A61M 16/10* (2006.01)

(52) U.S. Cl.
CPC ............ *A61M 5/002* (2013.01); *A61M 5/007* (2013.01); *A61M 5/19* (2013.01); *A61M 5/315* (2013.01); *A61M 25/0108* (2013.01); *A61B 8/0841* (2013.01); *A61M 16/06* (2013.01); *A61M 16/10* (2013.01); *A61M 2005/006* (2013.01); *A61M 2210/125* (2013.01)

(56) References Cited

U.S. PATENT DOCUMENTS

| | | | | |
|---|---|---|---|---|
| 6,302,574 | B1* | 10/2001 | Chan | A61B 17/8825 222/137 |
| 6,450,963 | B1* | 9/2002 | Ackerman | A61B 8/481 600/459 |
| 8,167,280 | B2* | 5/2012 | Chomas | B01F 5/0682 239/8 |
| 8,679,051 | B2* | 3/2014 | Keenan | A61K 49/223 424/9.52 |
| 2011/0087173 | A1* | 4/2011 | Sibbitt, Jr. | A61B 10/0233 604/207 |
| 2011/0166531 | A1* | 7/2011 | Stroumpoulis | A61M 5/19 604/191 |
| 2013/0221553 | A1* | 8/2013 | Chen | C08J 11/04 264/8 |

OTHER PUBLICATIONS

Hagen et al., "Incidence and Size of Patent Foramen Ovale During the First 10 Decades of Life: An Autopsy Study of 965 Normal Hearts", Mayo Clin Proc, vol. 59, pp. 17-20, Jan. 1984.
Thompson et al., "Paradoxical Embolism", Quarterly Journal of Medicine, vol. 23, Jan. 1930, pp. 135-150, with Plates 4 and 5.

* cited by examiner

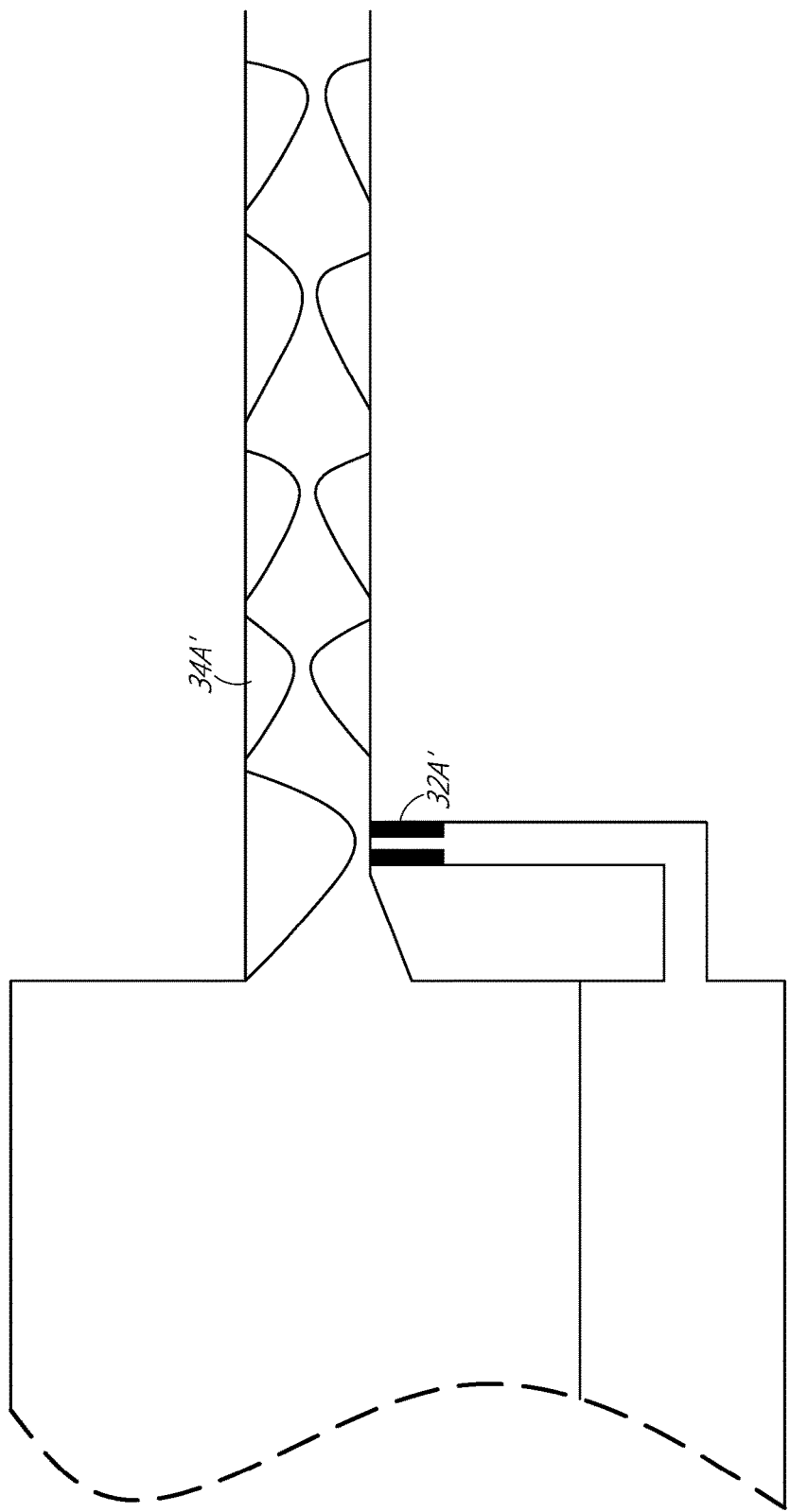

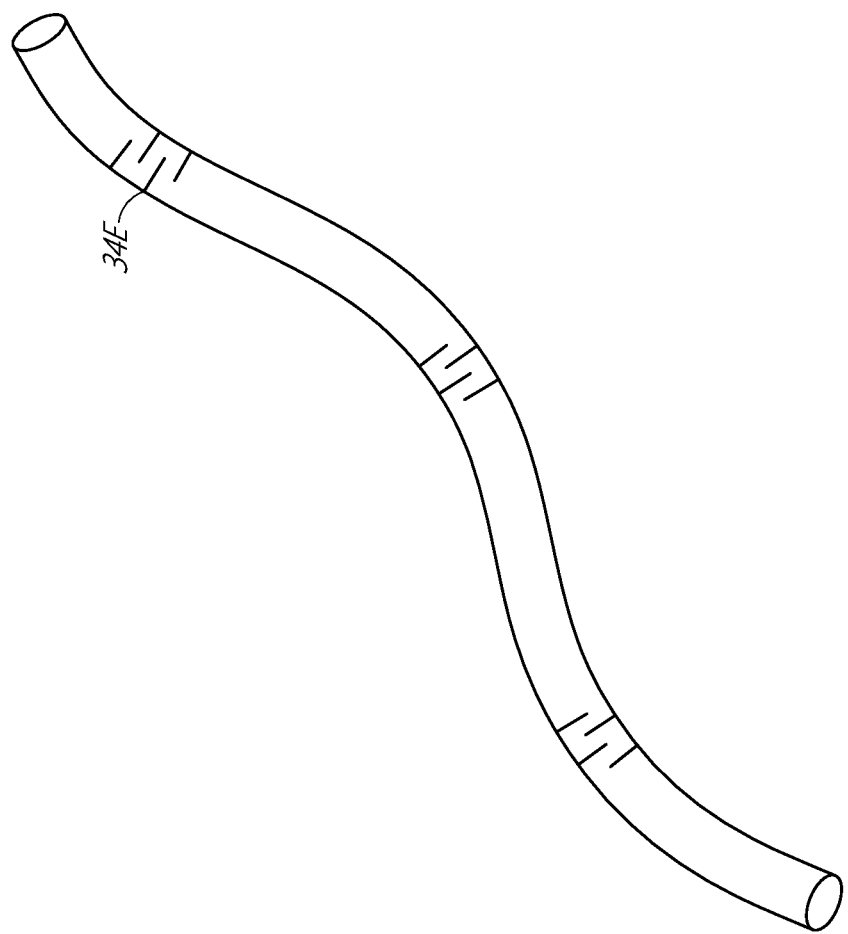

MEDICAL DEVICES AND METHODS FOR CREATING BUBBLES

PRIORITY INFORMATION

This application claims priority benefit under 35 U.S.C. §119(e) to U.S. Provisional Patent Application Ser. No. 62/296,434 filed 17 Feb. 2016 and entitled "MEDICAL DEVICES AND METHODS FOR CREATING BUBBLES"; and U.S. Provisional Patent Application Ser. No. 62/178,084, filed 31 Mar. 2015 and entitled "Dedicated device created to perform bubble study, to detect presence of patent foramen ovale (PFO) or atrial septal defect (ASD) in the heart. Given name to the device is 'B-Shoot'", the entirety of each hereby expressly incorporated by reference herein.

BACKGROUND

Field

This application relates to medical devices configured to generate bubbles. Such devices may be particularly useful for cardiovascular procedures, such as to detect the presence of Patent Foramen Ovale ("PFO"), Atrial Septal Defects ("ASD"), shunts in the heart, or other septal defects.

Description of the Related Art

The normal human heart, depicted in FIG. 1, can act as two biological pumps, side by side, sharing a common wall called a septum, and sharing one electrical network. The right side heart has two chambers known as the right atrium and the right ventricle. The left side heart also has two chambers known as the left atrium and the left ventricle. The right side of the heart receives deoxygenated blood from the body in its right atrium. The blood then goes into the right ventricle, which pumps the blood toward the lungs for oxygenation. From the lungs, oxygenated blood goes to the left atrium. From the left atrium the blood goes into the left ventricle, which then pumps the oxygenated blood through the body. In a normal heart, the left ventricle is the most powerful chamber capable of pushing the oxygenated blood into the body to meet body's metabolic demand.

The fetal heart, depicted in FIG. 2, is different from the adult heart. In a fetus, the lungs are still growing and not yet ready to receive blood for oxygenation. Two connections in the fetal heart help blood to bypass lungs of the fetus. One such connection is the Patent Foramen Ovale ("PFO"), which is a hole located in the septum that separates the left and right atria. This hole allows the blood to go from the right atrium to the left atrium bypassing the lungs. Another connection is the Patent Ductus Arteriosus ("PDA"), which is located between the pulmonary artery and the aorta. A majority of the blood is redirected through the PFO to bypass the lungs. However, a small amount of blood still enters the right ventricle, but is then redirected into the aorta through the PDA. With the help of both these connections, the PFO and the PDA, blood is prevented from going into immature fetal lungs.

Soon after birth the PFO and the PDA should close naturally, and blood should be directed toward the lungs of the newborn for oxygenation. From the lungs, the oxygenated blood goes to the left atrium and then to the left ventricle, from where it is pumped to fulfill the body's oxygen and other nutritional requirements.

Unfortunately, in 27% to 35% of people the PFO fails to close after birth (See, Attaran, Robert R., Imran Ata, Vijayasree Kudithipudi, Laura Foster, and Vincent L. Sorrell. "Protocol for Optimal Detection and Exclusion of a Patent Foramen Ovale Using Transthoracic Echocardiography with Agitated Saline Microbubbles." *Echocardiography* 23.7 (2006): 616-22. Web). This condition may be associated with numerous medical problems, including, but not limited to stroke, paradoxical embolism, cryptogenic stroke, and migraines. If blood clots developed in the veins detach, they normally travel to the right side of the heart, from which they may continue up to the lungs. When a PFO, ASD, or other shunts or septal defects are present, depending on pressure conditions between right and left atriums, small clots may flow from the right atrium to the left atrium, thus allowing a clot to bypass the lungs. Any clot that bypasses the lungs and reaches the left heart poses a great risk of interfering with the blood supply to tissues and organs to which it flows. For example, when such a clot enters an artery in the brain it may cause a stroke. Thus, correct and timely detection of a PFO/ASD is critical in preventing potentially serious medical problems.

SUMMARY

Imaging techniques such as Trans Thoracic Echocardiography ("TTE") and Trans Esophageal Echocardiography ("TEE") can be used for detection of PFO and similar conditions. For example, the heart can be imaged using ultrasound while a mixture of air and agitated saline (for example, 9 ml saline and 1 ml of air), including bubbles of the air, is injected through a patient's Intra-Venous line ("IV"). The mixture of bubbles and liquid can be agitated, producing a cloudy substance. When the mixture of air and saline enters the right side of the heart, an ultrasound image of the right atrium and the right ventricle can show white brightness therein, caused by the bubbles. Normally, the left heart would appear dark due to absence of microbubbles, as depicted in FIG. 3. However, when a PFO is present, some bubbles may flow from the right atrium to the left atrium, and can be visualized on the left side of the heart, for example in the ultrasound image, as depicted in FIG. 4. Sometimes the presence of a PFO is clear, and can be seen easily on the ultrasound monitor. In other cases a Valsalva maneuver can be used, under which pressure conditions between the left and right atria are changed for a short period of time with the help of the patient's cooperation.

FIG. 5 shows an example device for performing this procedure. As shown, a 10 ml syringe full of saline is provided. Then, 1 ml of saline can be removed from this syringe, leaving 9 ml for use. Another 10 ml, empty syringe has its plunger pushed up to the mark of 1 ml, leaving 1 ml of air in the syringe. Then both of the syringes are connected with a three-way stop cock. The third port of the stopcock is connected to the IV of the patient. The IV side of the stopcock is turned off leaving an open connection between both the syringes: one filled with 9 ml saline and the other with 1 ml of air. The saline and air are then rapidly mixed by pushing plungers of both the syringes back and forth. Mixing is done rapidly and forcefully so a cloudy mix of agitated saline and air bubbles is created.

While the substance is being mixed, an Apical Four Chamber Image of the heart is captured with the ultrasound machine. A recording length of the clip is set to, for example, 15-20 beats. Because the bubbles can quickly dissipate, both the preparation and pushing of cloudy mix of agitated saline and air bubbles, and capturing ultrasound images should be done simultaneously. When the cloudiness of agitated saline and bubbles is appropriate, the following steps are performed rapidly and skillfully in such a way that there is minimal loss of time, to prevent loss of agitation and disappearance of bubbles prior to injection into the IV:

1. Push the entire bubble mixture into one of the syringes.
2. Open the three way stopcock connection between syringe with the agitated cloudy mixture and the port attached to the IV.
3. Push the cloudy mixture into the IV.
4. While first technician starts to inject the mixture, an echo technician begins recording images using the ultrasound machine simultaneously.

The entry of the cloudy mix into the right atrium is visualized on the ultrasound machine's monitor. Once the bubbles present in the cloudy mix fill the right atrium, they quickly move into and fill the right ventricle. In a normal heart, the echogenicity of the bubbles in the right heart can be seen on the ultrasound machine, whereas left atrium and left ventricle appear dark due to absence of bubbles. When an abnormal connection, such as a PFO or ASD is present, some bubbles might cross the septum in to the left atrium as well as the left ventricle. Thus, the appearance of bubbles in the left atrium or left ventricle is indicative of an abnormal shunt.

Unfortunately, the technique depicted in FIG. 5 can have certain drawbacks. For example, poor skill in creating the cloudy mix of agitated saline and air bubbles can cause a false-negative result. This risk is further heightened by a lack of consistency in the procedure, as the quality of the bubbles and the speed with which they are injected is highly variable, not only with the technique of the operator(s), but also over time as the bubbles dissipate. For example, different technicians may use varying ratios of air and saline solution, or may apply inconsistent amounts of pressure through the syringe. Further, the entire mixture is typically used, because the bubbles only last for a short period of time. Thus, if the results of the test are inconclusive, the test must be repeated in full, risking a volume overload to the patient's vascular system.

In an embodiment, a syringe can create as a cloudy mix of agitated saline and air bubbles to assist in diagnosing PFO or ASD in the heart, or shunting in the vascular system. The device uses three chambers to produce a cloudy mix. A first chamber holds saline solution, a second chamber holds air, and mixing with agitation of saline solution and air bubbles occurs in a third camber. This third chamber can be configured with various types of geometric structures that assist in agitation and mixing to produce a cloudy mix of agitated saline and air bubbles. The geometric structures may be one or more small holes to create bubbles. The geometric structures may also include porous material to produce air bubbles. This device can create the cloudy mix of agitated solution and air bubbles just prior to being injected into the patients IV, thus minimizing the destruction of bubbles and loss of agitation prior to entering the IV. Steps in other methods such as manually mixing the saline solution with air and switching three way stopcock to the correct port of the IV can be eliminated. Further, the device can produce a consistent mix upon pressing the plunger irrespective of the individual skills and tendencies of varying users. Even further, the test can be performed with less volume. For example, if a defect is detected with, for example, 4 mL of an available, there is no need to push the entire volume of 10 mL into the IV. Then, if for some reason additional imaging is desired, the remaining 6 mL can be injected immediately, without needing additional mixing or other procedures. This helps prevent unnecessary volume overload in the vascular system of the patient, by reducing the volume of fluid technicians use.

In a further embodiment, a dedicated device for detection of a Patent Foramen Ovale, Atrial Septal Defect, shunts in the heart, or other vascular shunts can include a first chamber, a second chamber, and a third chamber. The first chamber can be configured to hold liquid, the second chamber configured to hold gas, and the third chamber can be in communication with the first and second chambers. The third chamber can include small-scale geometric features configured to produce gas bubbles as liquid from the first chamber and gas from the second chamber simultaneously flow into the third chamber. The device can also include a device opening in communication with the third chamber such that a mixture of liquid and gas bubbles can flow out of the device opening. The device can also include a plunger configured to force the liquid and the gas simultaneously from the first and second chambers, through the third chamber to mix with each other and produce bubbles, and further through the device opening.

In a further embodiment, a device configured to create a mixture of gas bubbles in a fluid can include a first chamber and a second chamber. The first chamber can be configured to hold liquid, and the second chamber can be configured to hold gas. Further, a valve can separate the contents of the first and second chambers from mixing. The device can also include an output, in communication with the first and second chamber, such that the fluid and gas can flow through the output, out of the device. Small-scale geometric features can be included, that can produce gas bubbles as the liquid and gas flow from the first and second chambers and through the output. A plunger on the device can simultaneously force the liquid and gas past the valve to mix with each other, through the small-scale geometric features to produce gas bubbles, and through the output. The valve can prevent this mixing of the liquid and the gas prior to movement of the plunger.

In a further embodiment, a device configured to create a mixture of gas bubbles in a fluid includes a first chamber configured to hold fluid and a second chamber configured to hold gas. The device also includes a means for continuously generating a liquid and gas bubble mixture and advancing that mixture through tubing immediately upon creation of the gas bubble mixture, the gas bubble mixture being suitable for imaging the mixture within a human heart using ultrasound.

In a further embodiment, a method for imaging an interior of a body is provided. A bubble generating device can be attached to an intravenous line. The bubble generating device can include a first chamber configured to hold a liquid, a second chamber configured to hold a gas, and a plunger. Advancement of the plunger can simultaneously and continuously force the liquid and the gas from the first and second chambers to mix with each other and produce bubbles and flow through the device opening. This advancement of the plunger can then be used to cause the bubble mixture to flow through the intravenous line. The mix of bubbles and liquid inside a body can then be imaged using ultrasound.

In a further embodiment, a method for imaging an interior of a body is provided. A bubble mixture can be generated, having bubbles of a size between 10 microns and 200 microns. The mixture can also include sufficient bubbles for ultrasound imaging inside a human heart. The bubble mixture can be advanced through a tube at the same time as the same mixture is continuously generated.

In a further embodiment, a dedicated device for detection of a Patent Foramen Ovale, Atrial Septal Defect, shunts in the heart, or other vascular shunts can include a first chamber configured to hold liquid. The device can also include a second chamber in communication with the first chamber, the second chamber comprising small-scale geometric features configured to agitate a liquid flowing to the second chamber from the first chamber. A device opening can be in communication with the second chamber such that the agitated fluid can flow out of the device opening. Further, a plunger can be configured to simultaneously force the liquid from the first chamber, through the second chamber to become agitated, and further through the device opening.

BRIEF DESCRIPTION OF THE DRAWINGS

Further objects, features and advantages will become apparent from the following detailed description taken in conjunction with the accompanying figures showing illustrative embodiments, in which:

FIG. 7C is an enlarged cross-sectional view of the distal portion of the device depicted in FIG. 7A.

FIG. 8 is a cross-sectional view of a tube that can be attached to the devices described herein, and includes small-scale features.

DETAILED DESCRIPTION

FIGS. 6, 6A-6D depict a device 1 that generates a bubble mixture that can optionally have a cloudy consistency. As discussed further below, the bubbles can be air bubbles formed in a saline solution. The bubbles can, in some embodiments, be "microbubbles", small enough to show-up on a standard ultrasound machine in a medical setting, yet large enough to not pass through the lungs.

The device 1 can be a dedicated device that assists detecting a PFO, ASDs in the heart, or abnormal shunting in the vascular system. However, other applications are also possible, such as for detecting other features or use with other animals. As another example, the device can assist in the placement of a catheter at an appropriate place during pericardiocentesis, such as by injecting a mixture that can be imaged to indicate the location of a needle and/or catheter. Further, although the device 1 can be a medical device (and thus can be sterilized and otherwise made suitable for medical use), this may not be necessary for certain applications. In some embodiments, the device 1 can also be prepared and delivered in an assembled and loaded state, within a packaging, such that a user can use the device immediately upon opening the packaging.

Figure 1:
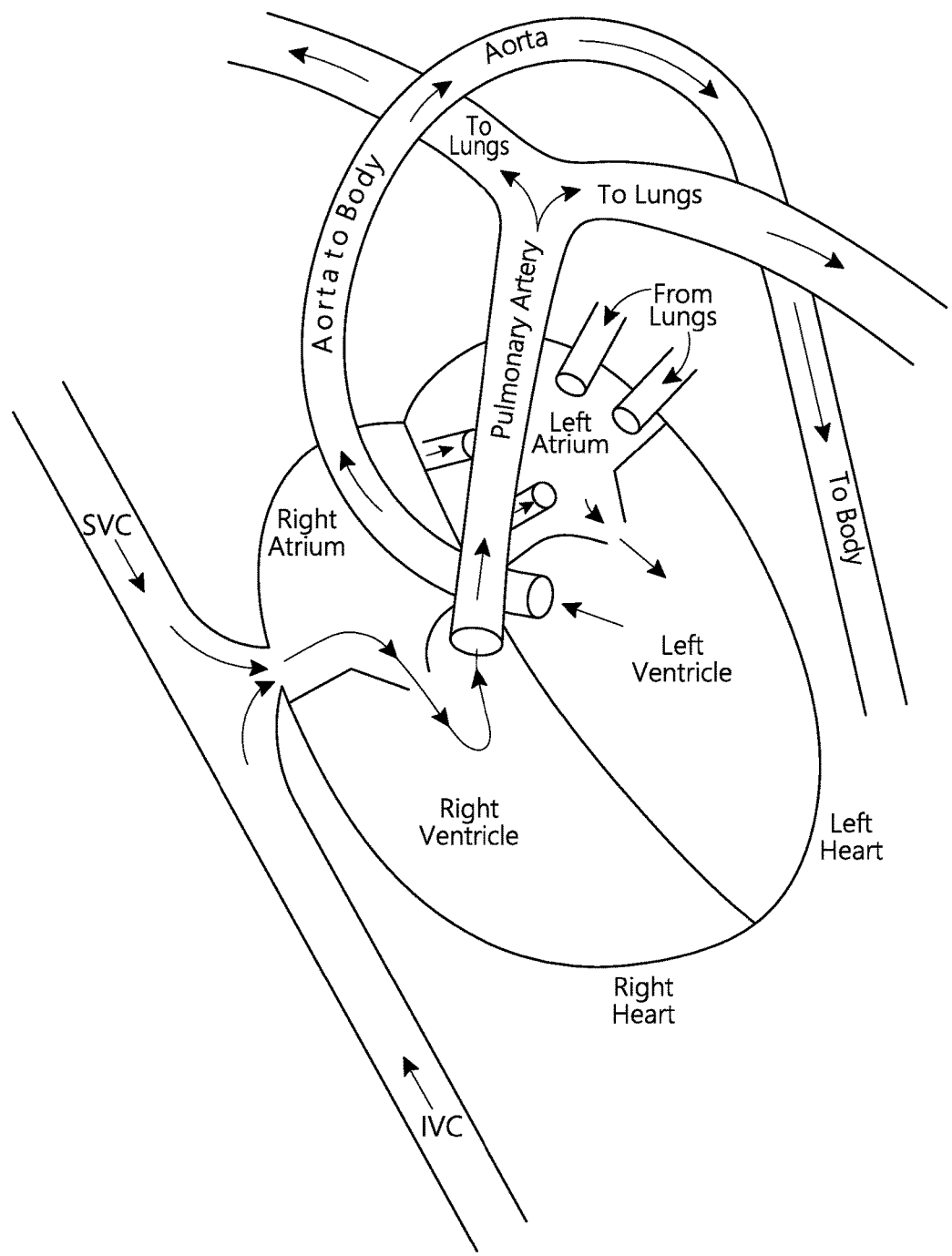
FIG. 1 depicts blood circulation in a normal human heart.
Figure 2:
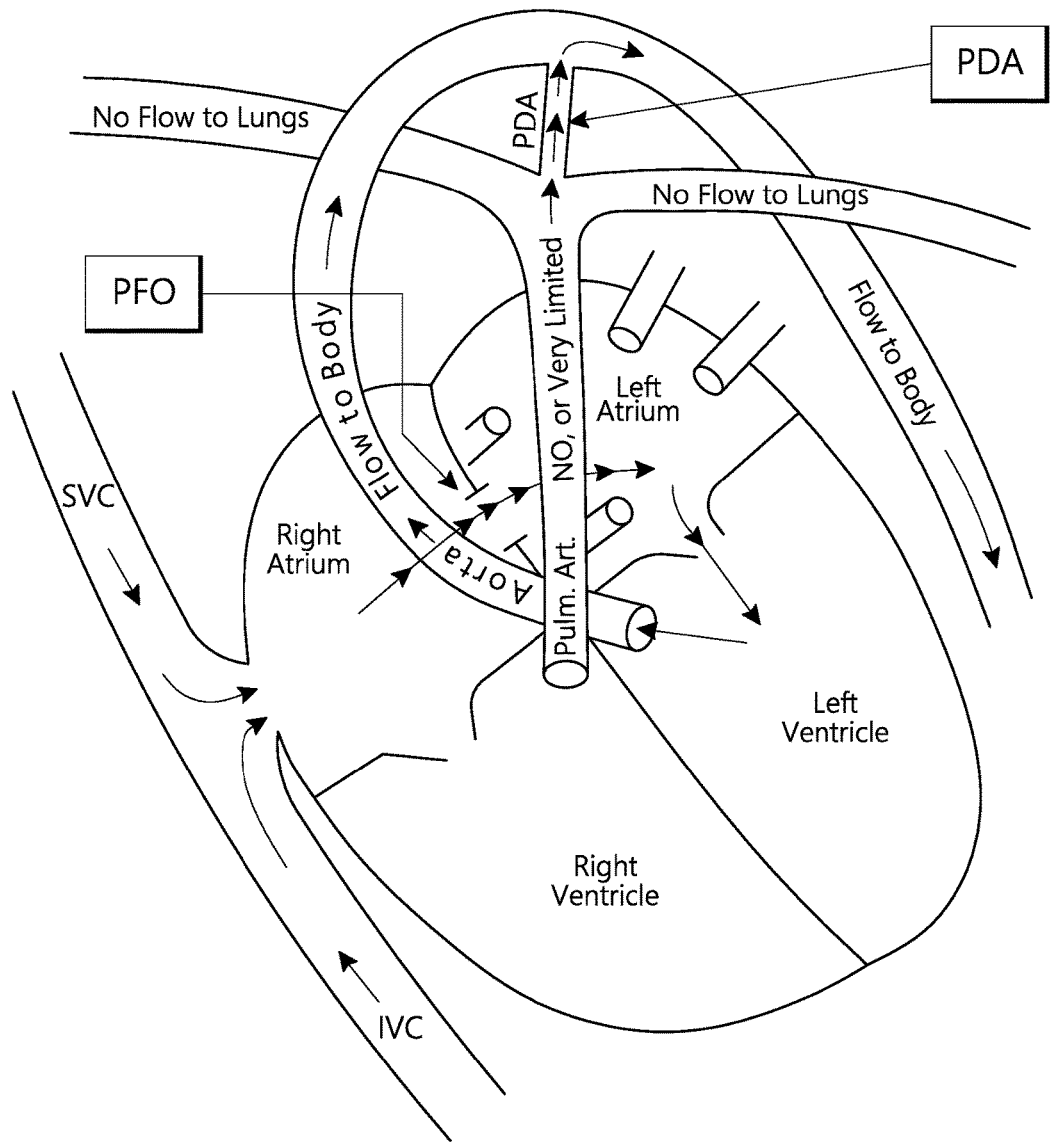
FIG. 2 depicts blood circulation in a fetal heart, or otherwise in the presence of a PFO and PDA in an adult heart.
Figure 4:
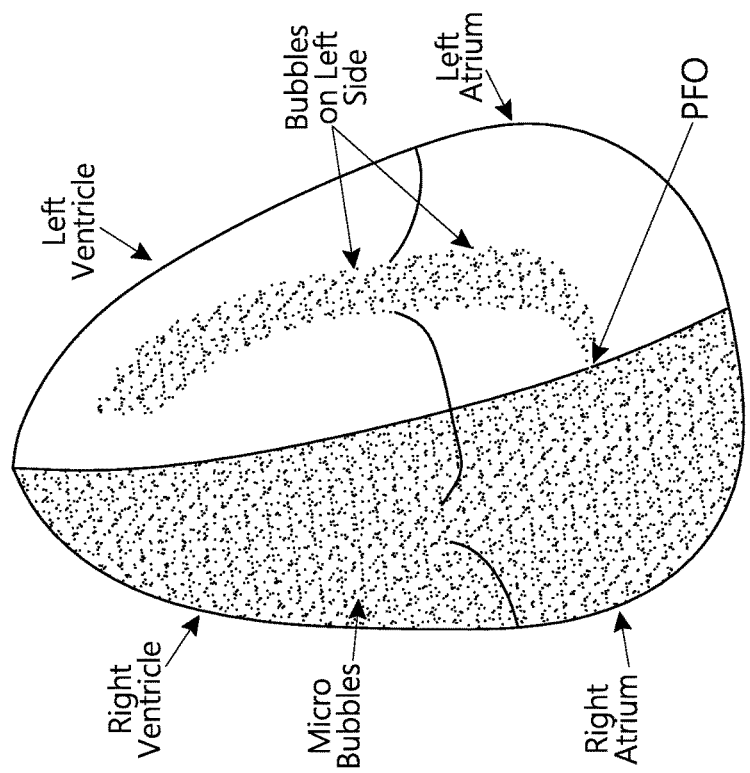
FIG. 4 represents an ultrasound image of a human heart in the presence of a PFO or other septal defects.
Figure 3:
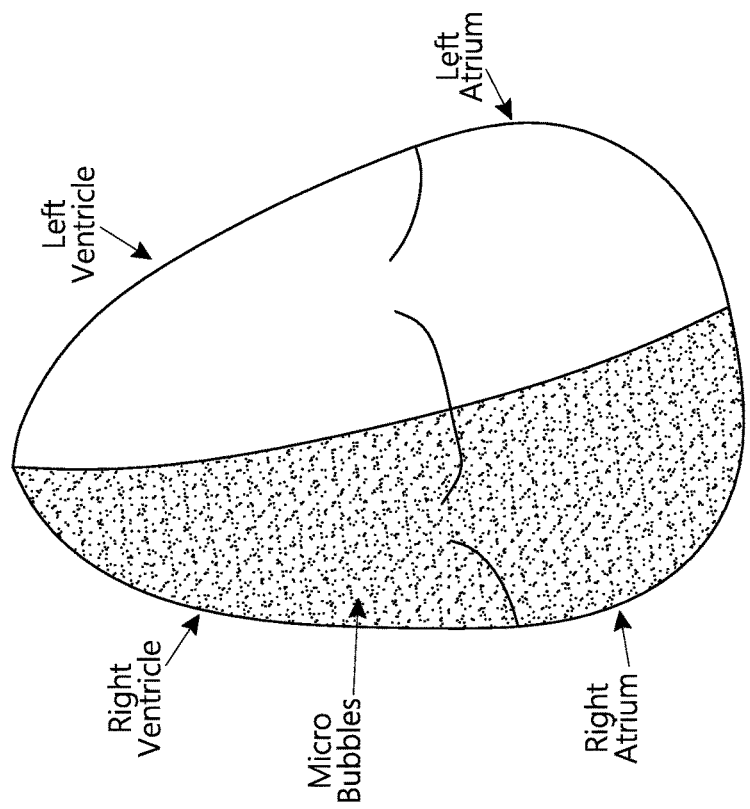
FIG. 3 represents an ultrasound image of a normal human heart after injection of a cloudy mixture of agitated saline and air bubbles.
Figure 5:
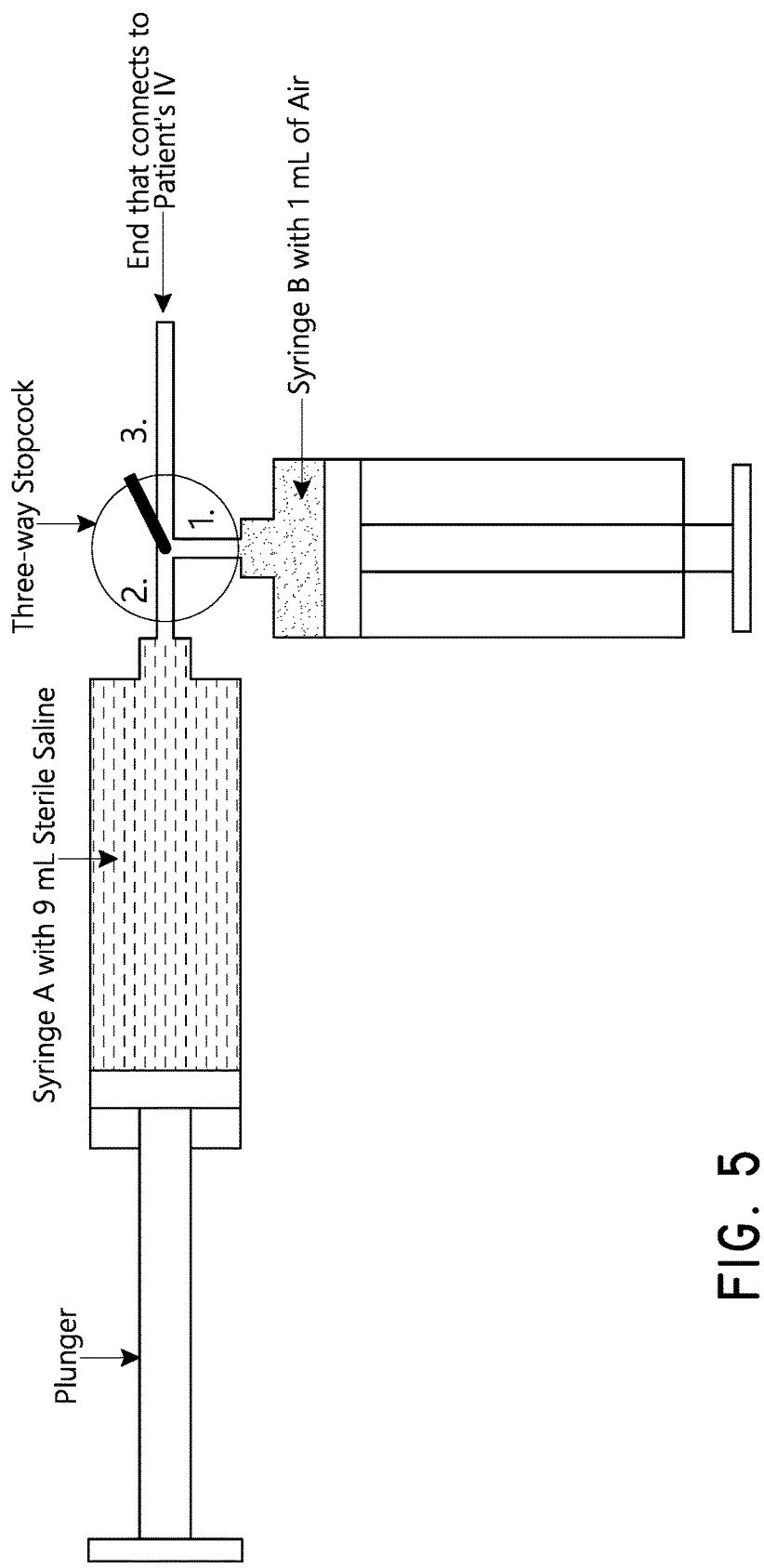
FIG. 5 depicts a system for injecting a bubble mixture into a human.
Figure 6:
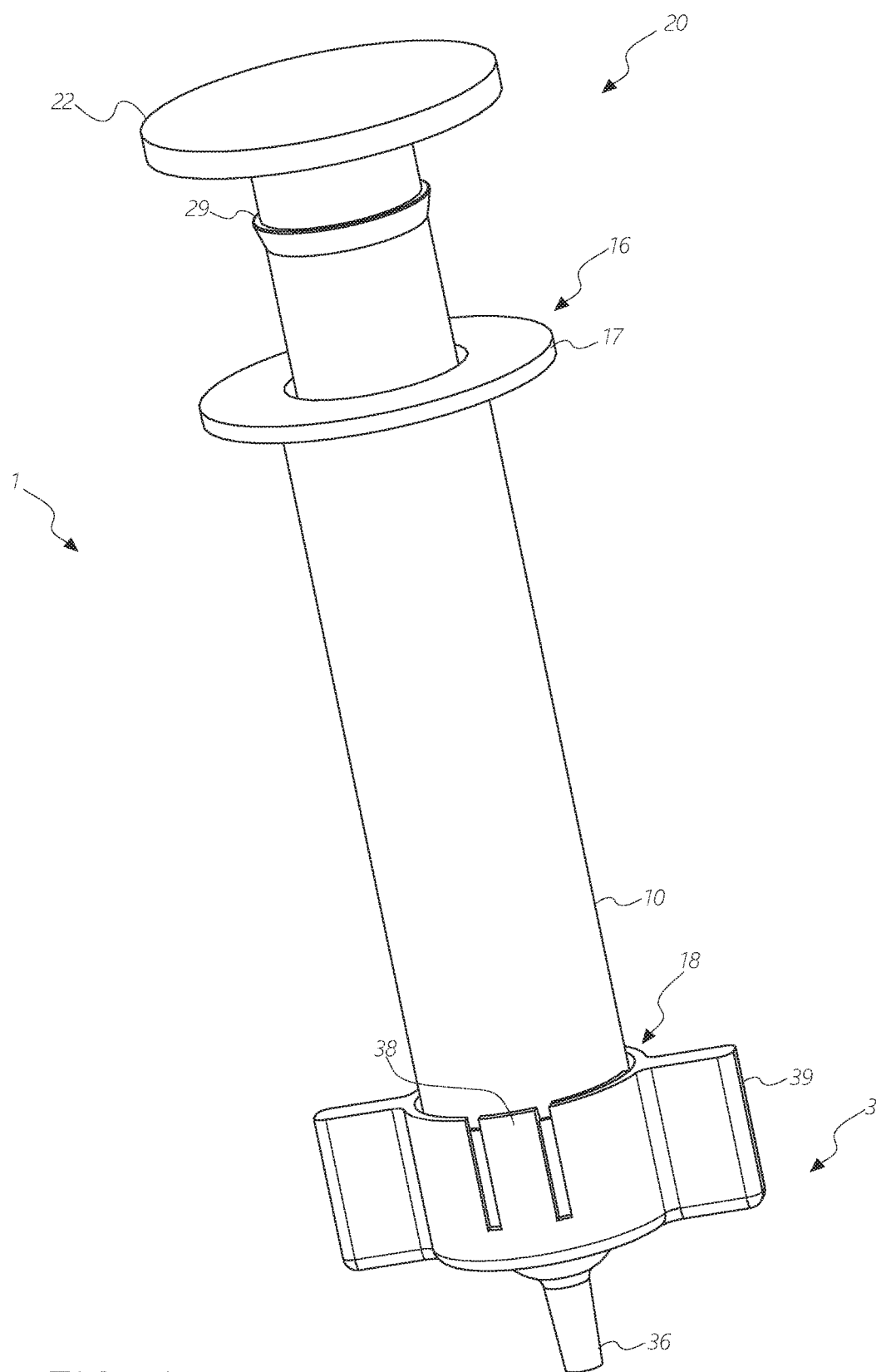
FIG. 6 is a perspective view of an embodiment device for creating and delivering a solution and air bubble mixture.

As shown in FIG. 6, the device 1 can include a plunger 20 at a proximal end and an output 3 at a distal end. Advancement of the plunger 20 can cause a cloudy mix of bubbles to be created and emitted from the output spout 3. The output spout 3 can be connected to the IV of the patient with common connection types such as luer-lock connections, although other connections can be made using threaded connectors, clasps, or other devices. Further, the output spout 3 can include an interior taper at its distal end, which can modulate the flow rate of solution through the output spout.

Figure 6A:
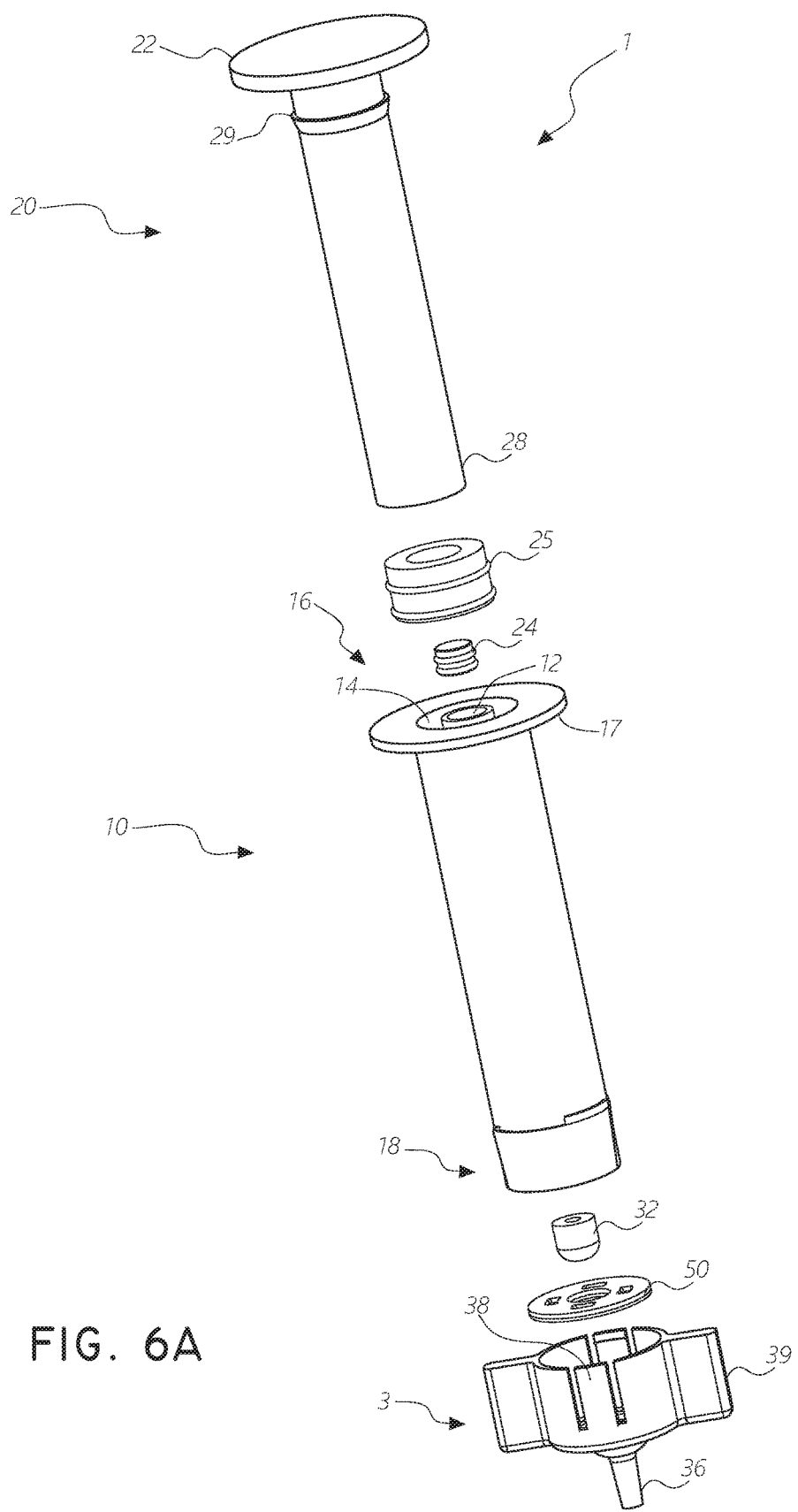
FIG. 6A is an exploded view of the device of FIG. 6.

A main body 10 can be disposed between the output spout 3 and the plunger 20. As best shown in FIG. 6A, the output spout 3 can include locking features, such as locking arms 38, that can attach the output 3 to a distal end 18 of the main body 10. As shown, the main body 10 can include a circumferential ridge near its distal end that can receive the locking arms 38, such that the arms can hold onto the ridge, thus holding the output spout 3 to the main body 10. Grooves can also be provided through the ridge, such that the arms can easily pass through and then twist to lock, forming a twist-lock mechanism. Other locking features are possible, such as a threaded connection, latches, clamps, etc.

The output spout 3 is additionally shown as having wings 39. The wings 39 can extend radially from the center of the output spout 3. The wings 39 can thus serve as handles for the output spout 3, facilitating handling of both the spout and the entire device 1 when connected. The wings 39 can also facilitate twisting between the output spout 3 and the main body 10, to facilitate alignment and attachment.

Figure 6B:
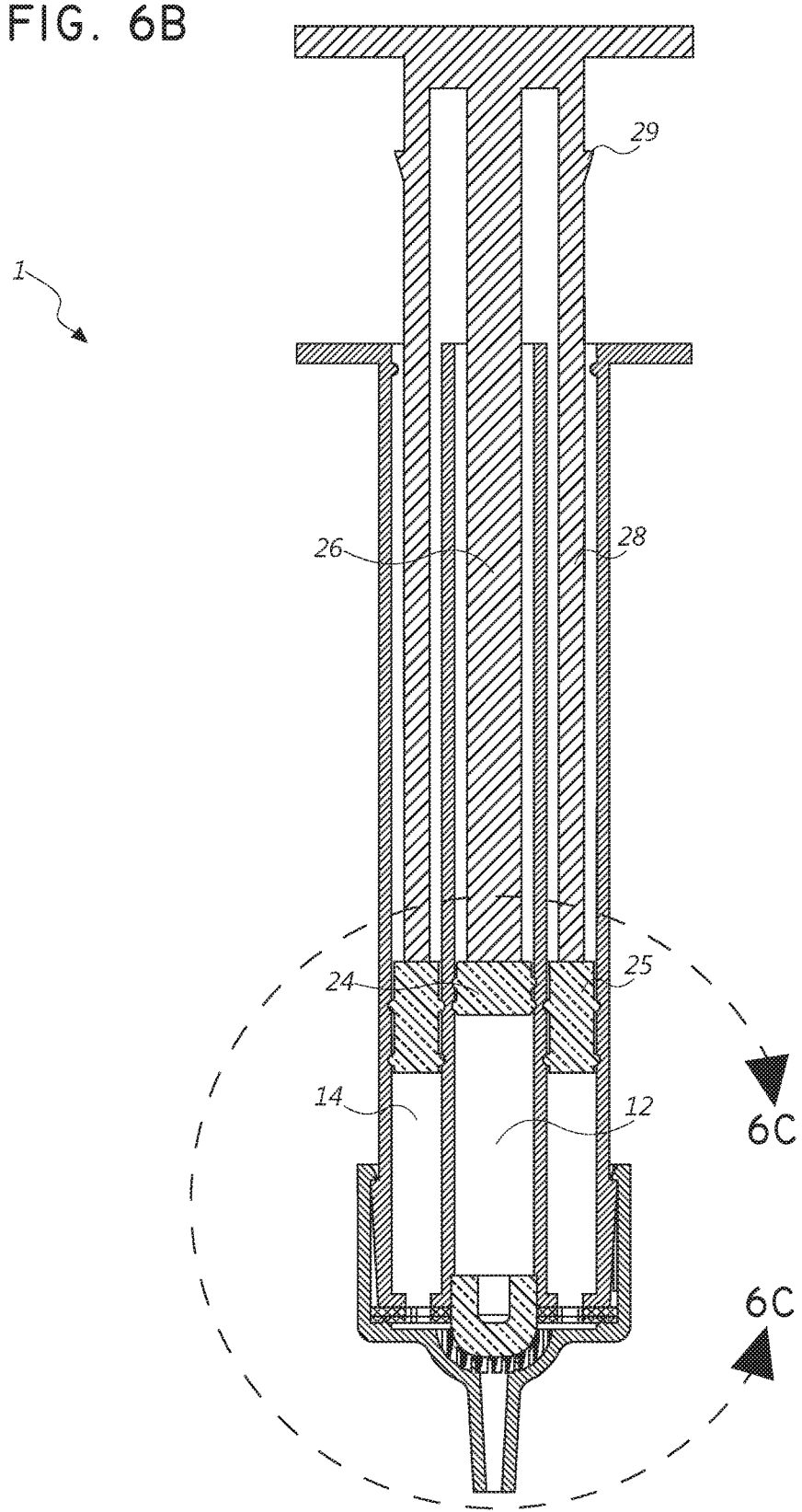
FIG. 6B is a cross-sectional view of the device of FIG. 6.
Figure 6C:
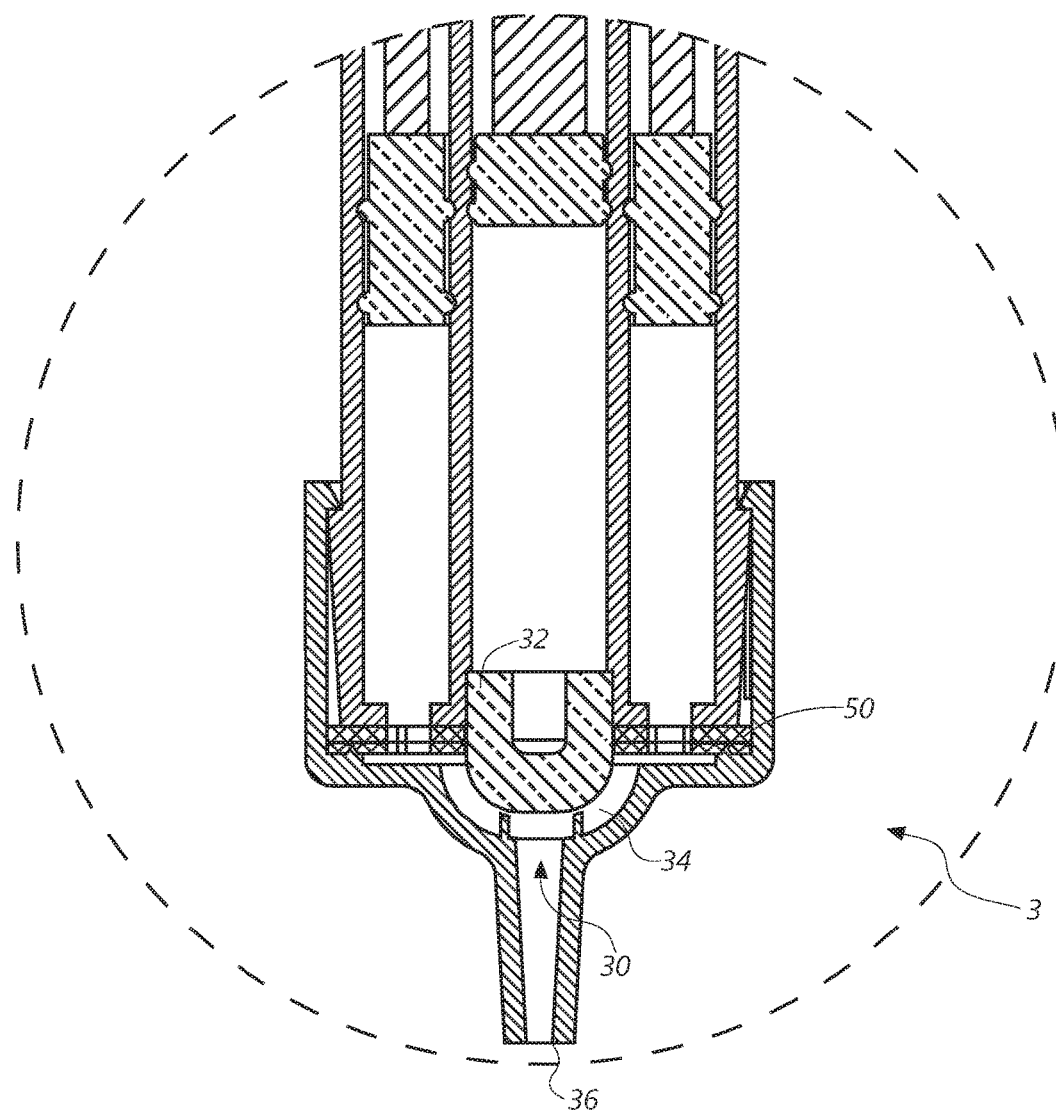
FIG. 6C is an enlarged cross-sectional view of a distal portion of the device of FIG. 6B.
Figure 6D:
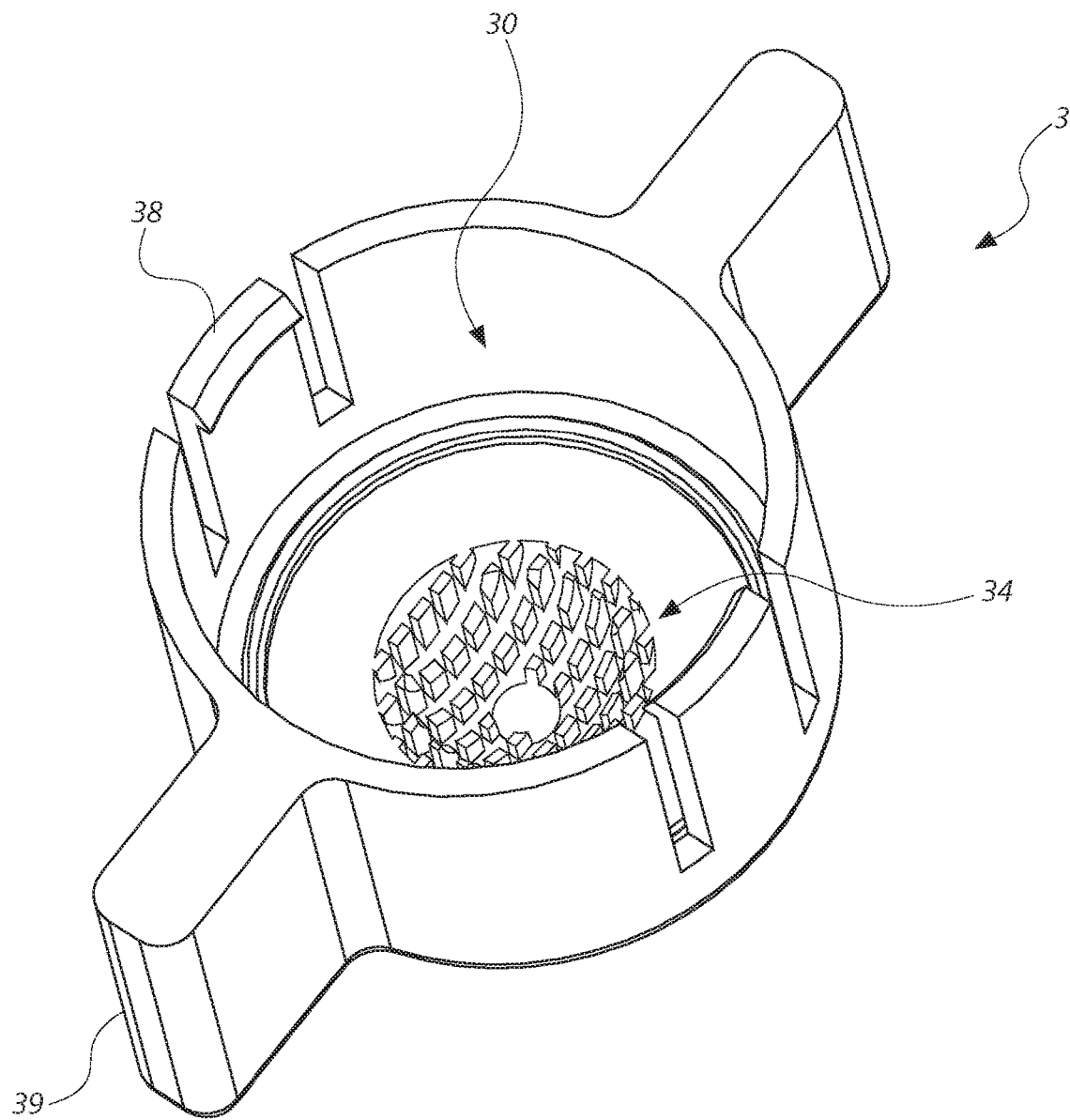
FIG. 6D is a perspective view of the inside of the output spout of the device of FIG. 6A.

As best shown in FIGS. 6C and 6D (and described further herein), the output spout 3 can also at least partially form a bubble chamber 30. Thus, the output spout 3 can promote the formation of bubbles in the solution. However, the chamber can also be formed by other features such as the main body, a valve, and a porous material, and the cloudy mix of bubbles can also be formed by other features.

The main body 10 can have a generally tubular structure forming two parallel chambers, as best shown in FIG. 6B. The depicted embodiment shows two chambers: a first chamber 12 disposed along a central axis of the main body 10, and a second chamber 14 annularly surrounding the first chamber 12. However, other arrangements of the chambers are possible.

The chambers can also be arranged generally parallel and adjacent. Thus, the plunger 20 can push through both of the chambers 12, 14 at the same time. The main body 10 can also include openings to facilitate the filling of the chambers 12, 14 with desired substances, such as saline or air. In the depicted embodiment, the saline and air can enter the main body 10 from the proximal end 16, when the plunger is removed. However, in other embodiments other sealable openings such as valve systems can be provided such that the chambers can be filled from other places such as a lateral opening. Thus, the plunger 20 need not be removed prior to filling the chambers.

The main body 10 is additionally depicted as including a flange 17 at its proximal end 16. The flange 17 can be used as support by fingers to hold the body 10 when the thumb is advancing the plunger 20 distally towards the output spout 3. Optionally, in some embodiments, the flange 17 can abut an annular flange 22 of the plunger 20 when the plunger is fully inserted into the main body 10 to stop the plunger. In other embodiments, both flanges can be used for gripping support. This insertion of the plunger 20 into the main body 10 can also push the substances in the chambers 12 and 14 through the main body 10, as further discussed herein. This pushing can be facilitated by first and second seals 24 and 25. The first seal 24 can enter the first chamber 12, and be pushed by a first plunger portion 26 of the plunger 20 to push a substance through the first chamber. Similarly, the second seal 25 can enter the second chamber 14, and be pushed by the second plunger portion 28 to push a substance through the second chamber.

The seals 24, 25 and the plunger portions 26, 28 can be generally shaped to match the first and second chambers 12, 14. Thus, in the depicted embodiment, the first seal 24 and the first plunger portion 26 can be generally disposed along a central axis of the plunger 20. Similarly, the second seal 25 and the second plunger portion 28 can annularly surround the first seal 24 and plunger portion 26. The seals 24, 25 can be formed from a resilient material such as a rubber, neoprene, plastic, or other materials configured to prevent substances within the first and second chambers 12, 14 from flowing past the seals. Thus, as the seals 24, 25 are advanced through the chambers 12, 14, the substances in each chamber are compelled forward. Further, in some embodiments the seals 24, 25 can be attached to the plunger portions 26, 28, such that they can also be removed from the chambers 12, 14, with the plunger 20. Further, in some embodiments the seals 24, 25 can abut features at the end of the chambers 12, 14, such as the porous material 32 or the gasket 50, to stop the advancement of the plunger 20.

The plunger 20 can also optionally include a locking ridge 29. The locking ridge 29 is depicted as being along an exterior of the plunger 20, along the wall of the second plunger portion 28, as best shown in FIG. 6A. The locking ridge 29 can have a wedged shape, such that it can slide over a corresponding raised portion on the interior of the second chamber 14. The plunger 20 can then lock within the main body 10 when the plunger has been fully-advanced. Other locking features can also be used, such as by including latches or other structures on other portions of the plunger 20 and the main body 10. For example, in some embodiments, the locking features can be disposed on an exterior of the plunger 20 and an exterior of the main body 10. The locking features can prevent proximal motion of the plunger 20. The locking features can also facilitate one-time-use of the device 1.

As the plunger 20 is advanced distally through the main body 10, the substances in the chambers 12, 14 can be advanced forward. The two chambers can include different substances, such as air in the first chamber 12 and saline fluid in the second chamber 14. The ratio of saline to air can vary; for example, a ratio of saline to air can be approximately 8:2, 9:1, 9.5:0.5, 9.75:0.25, or 9.9:0.1. The volume of saline solution can also vary, being for example no more than 30 mL, no more than 20 mL, no more than 10 mL, no more than 5 mL, or no more than 3 mL. The saline solution can be at least 5 mL. Similarly, the volume of air can also vary, being no more than 3 mL, no more than 2 mL, no more than 1 mL, no more than one-half mL, or no more than one-quarter mL. The air can be at least one-quarter mL. The main body 10 and its chambers 12, 14 can optionally be sized to accommodate substantially only the desired volumes of substances. Sufficient air and saline solution can be used to ensure the effectiveness of the cloudy mix for acquiring reasonably echogenic images as discussed further herein.

Other substances can also be used. For example, instead of air, a specific gas can be used, such as a biologically inert gas, non-toxic gas, or a gas mixture. Further, the arrangement of the substances can be reversed. Even further, additional chambers can be included that may also include air or saline fluid, or alternatively may include another substance to be mixed. For example, patient's blood could potentially be used instead of or in addition to the saline to create an agitated cloudy mix. In other embodiments, chamber(s) may be excluded from device 1. For example, when the device is to be used for pediatrics purpose it can optionally not include the air chamber. The saline solution can have a concentration safe for use in humans, such as approximately 9 grams of NaCl per liter of water. In other embodiments, the saline may have a lower concentration of salt, include other ingredients such as dextrose, or vary in other ways appropriate for medical use.

The plunger 20, including two plunger portions 26, 28, can facilitate the propulsion of substances from both of the chambers 12, 14, at the same time, with a single motion. This can help ensure a consistent and constant relative concentration of each substance in the mixture throughout operation. However, in other embodiments separate plungers for each chamber can be provided to act as a single plunger. The separate plungers can potentially be arranged to facilitate advancement of both plungers at a similar rate. For example, handles of the plungers can be directly adjacent to each other, such that a single hand can easily push both plungers forward simultaneously. Further, multiple plungers can be optionally attached, for example using a reversible locking mechanism, such that a user can choose between locking the plungers together so they advance simultaneously or leaving them free to move independently. The plungers could be pulled back separately drawing desired substances to fill different chamber independently.

Further, in some embodiments a spring or other pressure mechanism can be mounted with the plunger to push the plunger to propel the substances from the chambers. The spring can be pre-loaded and released by an actuator such as a switch to begin the propulsion of the substances. Advantageously, the spring can ensure a repeatable flow rate and reduce the effort required by a user. Similarly, in some embodiments one or more of the chambers can be pressurized and an actuator can open the chamber, such that the substance can exit at a reliable rate and with less effort from the user. Further, another actuator can be included that can open or close the output spout 3 or another portion of the device that affects the flow rate, such that the flow rate can be easily adjusted. In further embodiments, an actuator can open or close outlets from the first or second chambers, to adjust the proportions of liquids and gases.

As the substances move distally through the main body 10, they can be forced into a bubble chamber 30. As best depicted in FIGS. 6C and 6D, the bubble chamber 30 can be substantially defined by the interior of the output spout 3. However, other features of the device 1, such as the main body 10 or outlets from the first and second chambers 12, 14, can also help to define the bubble chamber 30. As the substances from the first and second chambers 12, 14 enter the bubble chamber 30, bubbles can be created, such that the resulting substance is a cloudy mixture of agitated saline and air bubbles. As discussed above, the output spout 3 can then direct the solution onward, for example to additional tubing, an IV of the patient, another device, etc.

The bubbles can form in the bubble chamber 30 through a variety of ways. For example, the bubble chamber 30 can include small-scale geometric features configured to promote bubble formation and shearing. In some embodiments a screen including small holes can be provided near the end of a chamber containing gas in the main body 10, such as the first chamber 12. The small holes can thus promote the formation of bubbles at the time of mixing. The holes can optionally be between approximately 10 microns and 1000 microns in size. The resulting bubbles can have variable sizes that are optimal for creating a cloudy mix that can be viewed on an ultrasound machine. For example, the bubbles exiting the device can optionally have an average size of approximately 30 microns, between 20 and 40 microns, between 10 and 100 microns, or between 10 and 200 microns. Such bubbles may be sufficiently large to not pass the lungs. The screen, small hole(s), or porous material can be located, for example, at a distal end of the main body 10, near a distal end of the main body 10, inside the output spout 3, or otherwise generally near a point where a gas and liquid mix together.

Similarly, in some embodiments the small-scale geometric features can be in the form of a thicker porous material such as polypropylene, stainless steel, aluminum, titanium, gold, silver, and other medical grade metals and plastics or other sponge-like materials. An example of a porous material 32 is best shown in FIGS. 6A, 6B, and 6C. As shown, the porous material 32 can be mounted to the main body 10, but extend into the bubble chamber 30. Thus, gas from the first chamber 12 must pass through the porous material to enter the bubble chamber. In some embodiments, a screen or other body with small holes can be provided in an arrangement similar to the porous material to create bubbles.

Even further, in some embodiments the small-scale geometric features can be agitation features 34 such as protrusions (depicted as fins) that extend into the bubble chamber 30 to agitate the substances' flow and shear air bubbles as they pass through the chamber. This agitation can potentially create a cloudy mix of agitated saline and air bubbles. In additional embodiments, these features for creating bubbles can be combined, such as with a screen/porous material and agitation features 34. Further, the agitation features 34 can optionally include their own holes, further facilitating the creation of bubbles. Advantageously, the agitation features 34 can facilitate the formation and shearing of bubbles and also help mix the bubbles into the resulting substance to create a substantially consistent cloudy mixture. The bubble chamber 30 can have a shape such that the substances are forced to flow substantially through the agitation features 34, and not around the agitation features 34.

The bubbles dissipate quickly over time, so it may be preferable to create them as close to the point of exit as possible. Formation of the bubbles near the output spout 3 (or in the output spout 3) can help preserve the cloudiness of the mixture as it exits the device. Advantageously, the bubbles can be created continuously by the small-scale features, as the mixture exits the device 1. However, it is also possible to create the bubbles at other portions of the device 1. For example, in some embodiments a tube (such as an IV line) attached to the output 36 can include small-scale agitation features 34E, as shown in FIG. 8. Thus, the bubble chamber 30 can be extended even further, and closer to exit from the device, further preserving bubbles created.

The device 1 can additionally include one or more holes between the second chamber 14 and the bubble chamber 30, forming a portion of the bubble chamber. As depicted best in FIGS. 6A, 6B, and 6C, these holes can be included as part of a gasket 50, although they can also be provided as part of other features, such as the main body 10 or the output spout 3. The holes can permit the flow through the device 1, and in some embodiments the flow rate can be tuned using the size of the holes, frictional forces in the device 1, the size of the output spout 3, and other features, such that the cloudy mixture exits the device at a rate desirable (e.g., for use in detecting ASDs or other medical conditions) when a normal pressure (for example, the pressure applied by a normal person) is applied. In some embodiments, a set or system can include the device 1 and a variety of gaskets or other device components having varying sizes of holes, varying porous materials, or other varying geometric features that promote a faster or slower flow rate (and a potentially corresponding lesser or greater agitation or bubble formation). Thus, a user can easily adjust the flow rate according to their specific situation. Notably, these holes can also encourage bubble generation in the bubble chamber 30.

Figure 6E:
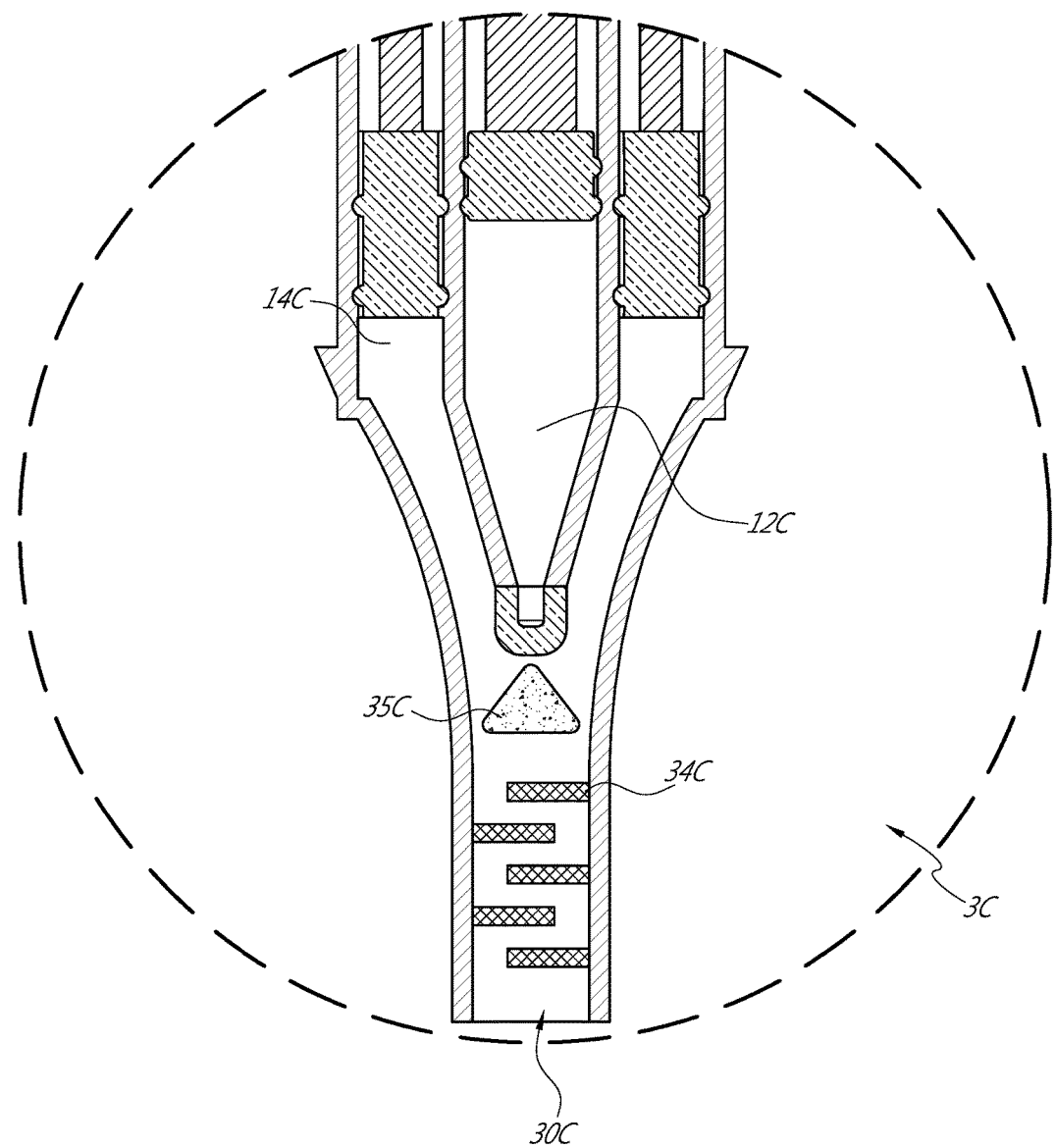
FIG. 6E is an enlarged cross-sectional view of a distal portion of a device similar to the device of FIG. 6C.

FIG. 6E depicts another embodiment of an output spout 3C, similar to the output spout 3 of FIG. 6, and capable of interacting with the rest of the device 1 in FIG. 6 in a similar way. Unless otherwise stated, the features in FIG. 6E can be similar to the features in FIG. 6C. As shown, the output spout 3C can include a diverter 35C in the shape of a cone (although other shapes are possible). The diverter 35C can be positioned to divert the flow of gas from the first chamber 12C outward such that they mix more with substances flowing from the second chamber 14C. Absent the diverter 35C, the gas bubbles could tend to flow straight forward, creating a less even distribution of bubbles throughout the flow. The diverter 35C can divert the bubbles from this flow path, promoting mixing and a more-even distribution of bubbles. Further mixing and agitation can be promoted using agitation features 34C.

Figure 7A:
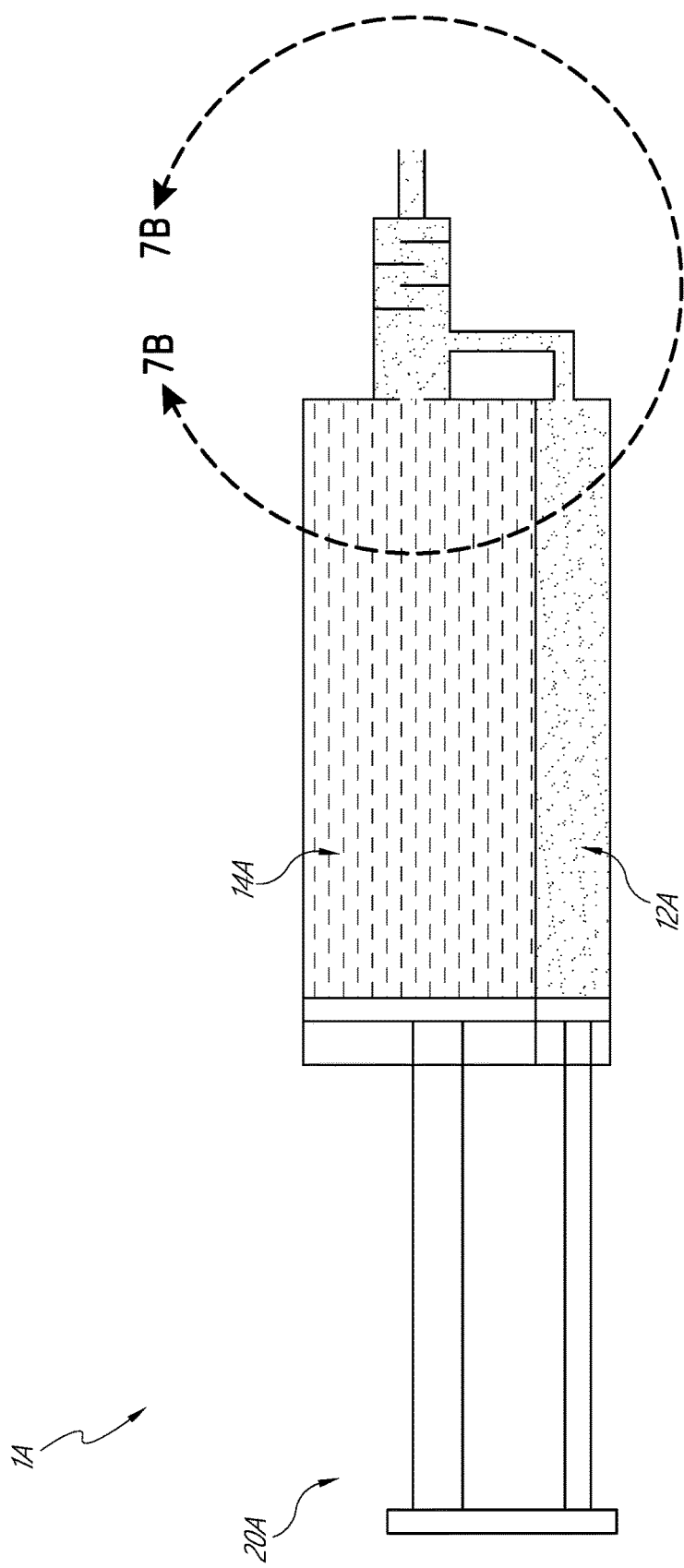
FIG. 7A is a cross-sectional view of another embodiment device for creating and delivering a bubble mixture.
Figure 7B:
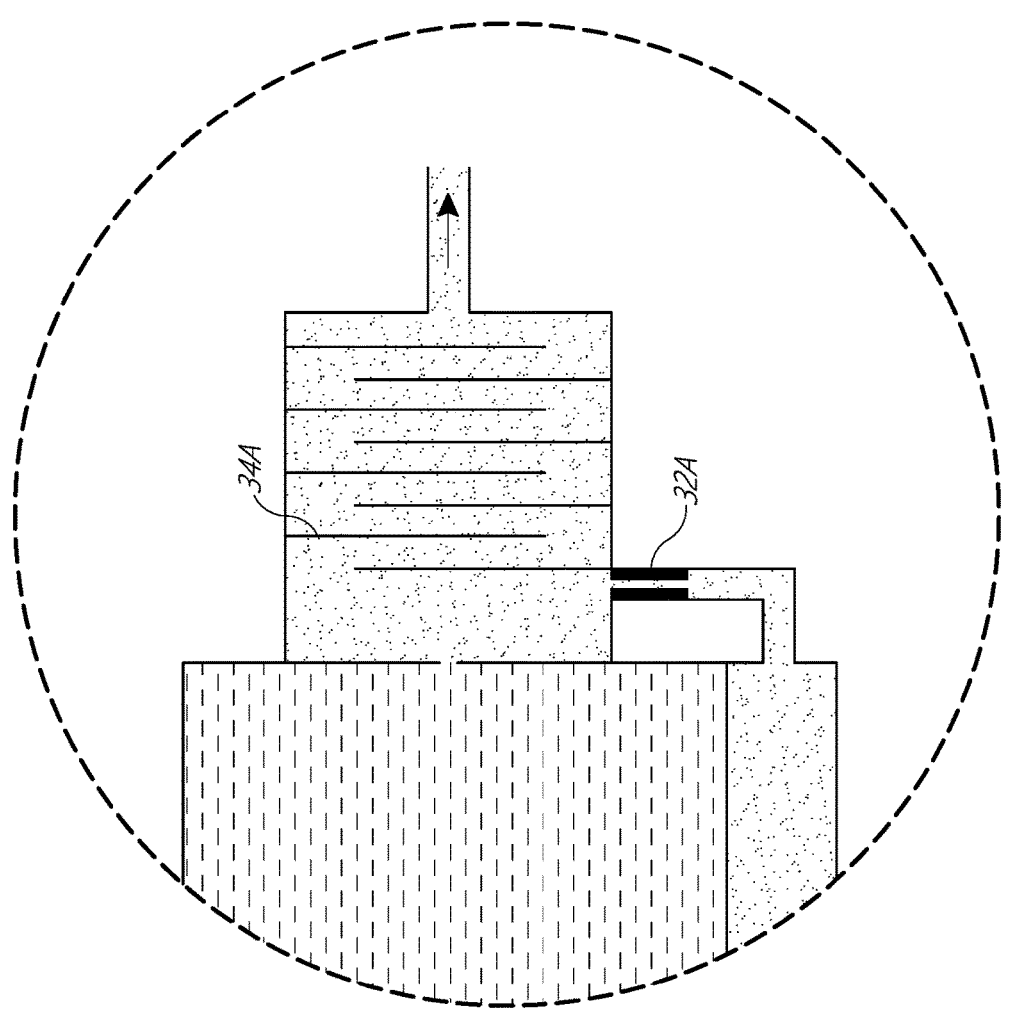
FIG. 7B is an enlarged cross-sectional view of the distal portion of the device depicted in FIG. 7A.

FIGS. 7A and 7B depict another embodiment bubble generating device 1A, similar to the bubble generating device 1 depicted in FIG. 6. Unless otherwise stated, the features in FIGS. 7A and 7B can be similar to the features in FIGS. 6, 6A, 6B, and 6C. For example, the bubble generating device 1A can include a common plunger 20A that pushes a substance out of first and second chambers 12A, 14A. However, as shown in FIG. 7A, the first and second chambers 12A, 14A can be disposed in a side-by-side arrangement. The first chamber 12A can have a smaller volume than the second chamber 14A, and can hold a gas such as air while a fluid such as a saline solution can be held in the second chamber.

As best shown in FIG. 7B, the output from the first chamber 12A can include one or more micro holes, or a porous material 32A, to create bubbles. Further, the bubble chamber 30A can include agitation features 34A extending from either side to increase agitation and mixing.

FIG. 7C depicts an alternative distal portion of device 1A, similar to that depicted in FIG. 7B. As shown in FIG. 7C, the porous material 32A' channels air to the bubble chamber 30. Geometric structures 34A' can create bottlenecks with small holes at the center of each structure. This can help create a cloudy mix of agitated saline and air bubbles using post stenotic turbulence. This type of turbulence may occur due to each bottleneck structure forcing the mixture to increase velocity due to a gradual decreasing volume for the flow as it approaches the small hole. The abrupt exposure to a relatively larger volume available right after exit from the small hole can create turbulence and a better cloudy mix.

Figure 7D:
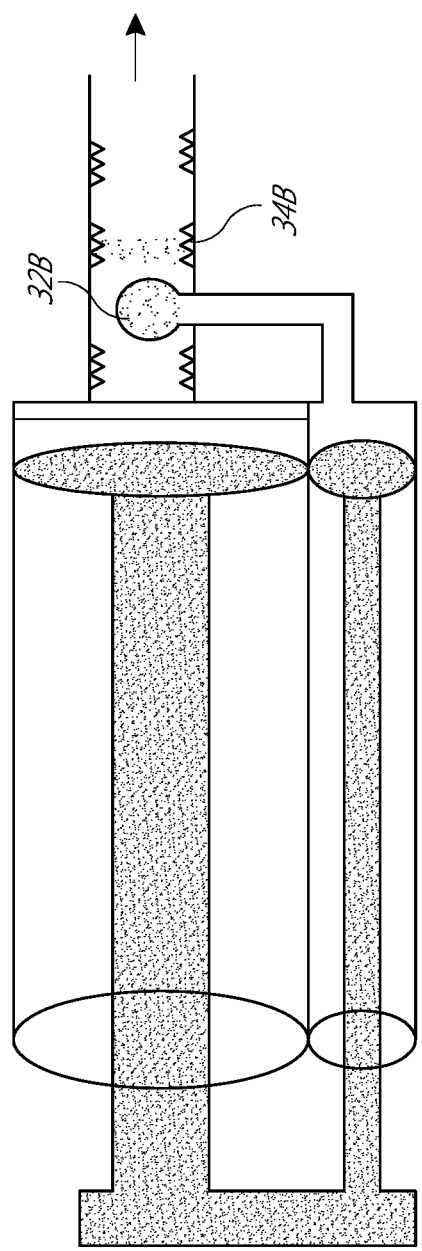
FIG. 7D is a cross-sectional view of a device similar to the device depicted in FIG. 7A.

FIG. 7D depicts an alternative distal portion of a device 1B, similar to that depicted in FIG. 7B. As shown in FIG. 7C, the porous material 32B can extend deeply into the bubble chamber 30C, in a manner similar to that depicted in FIG. 6C. Even further, the porous material 32B can overlap with the agitation features 34B, such that the bubbles created by the porous material can be injected directly into a turbulent flow.

Figure 7E:
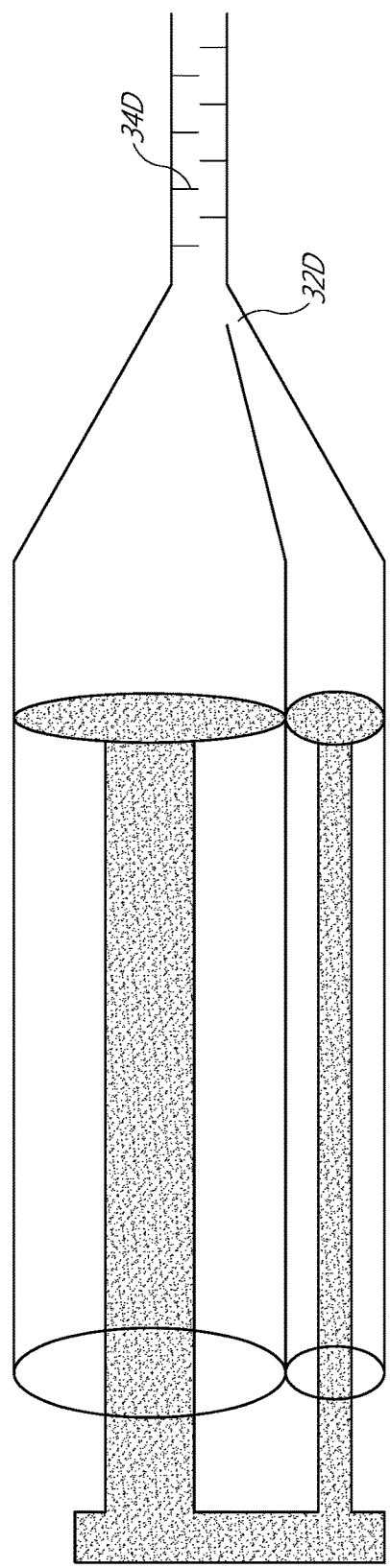
FIG. 7E is a cross-sectional view of a device similar to the device depicted in FIG. 7A.

FIG. 7E depicts another alternative distal portion of a device 1D, similar to that depicted in FIG. 7B. As shown, bubbles can be initially created by a single micro-hole 32D separating the chambers for a gas and a fluid. In other embodiments, there can be more than one micro-hole. Further bubble formation can then be encouraged with the agitation features 34D.

In additional embodiments, it may be desirable to include mechanisms to prevent the substances in the chambers 12, 14 from mixing prior to use. In some embodiments, the small holes can be sufficient to prevent mixing absent pressure applied (for example, from the plunger 20). However, a valve or other mechanism can also optionally be included to prevent mixing. For example, one or more of the chambers can optionally include a valve that can be opened manually, or alternatively can open automatically when a sufficient pressure is applied by the plunger 20, such as a check valve.

In some embodiments, this valve can be positioned between a chamber intended to contain a gas and the bubble-producing small-scale features. Thus, the device can potentially be filled with saline solution in the other chamber by pulling the plunger back, while the valve prevents the saline solution from entering the chamber intended to contain a gas. In some embodiments, a closeable hole may be provided to the chamber for gas, such that it can be filled by pulling back the plunger as the other chamber is being filled with saline solution.

It can also be possible to provide a valve between a chamber intended to contain a fluid and the bubble-producing small-scale features. In this situation, gas could flow freely between other portions of the device and the atmosphere, without concern about the fluid leaking out of the device. It will be clear that other arrangements of the valve are possible, such as a combination of the valves described herein.

Even further, in some embodiments the devices described herein can be prepackaged in an assembled or partially assembled state. For example, the device can be included in a packaging with a configuration as shown, for example, in FIG. 6, and can initially already have each chamber filled with the appropriate fluid/gas. In other embodiments, the devices can be included in a packaging with the plunger in a closed state, such that a user can potentially fill the device immediately by pulling the plunger back (or multiple plungers, either together or separately) while the output spout communicates with a desired substance. The packaging can be sealed and the device enclosed can be sterilized, such that a user can open the package and immediately use the device.

If the device is not prepackaged in a state ready for use, then a user can initially assemble the device, including putting together separate parts and loading one or more chambers with the appropriate fluid and/or gas. The output of the device can then be connected to tubing that has access to a body portion, such as a person's circulatory system, such as an intravenous line.

Additionally, imaging of a relevant portion of the person's body, such as the person's heart (particularly, an apical 4 chamber view of the heart) can be prepared. The imaging can be done, for example, using ultrasound imaging or another imaging system that can detect the presence of bubbles.

Once the imaging of the heart is ready and the device is ready, a user can advance a single plunger on the device distally, to push both the liquid and the gas distally through the device. In some embodiments, multiple plungers can be used, and these plungers can optionally be attached such that they are advanced together as one plunger to ensure a constant ratio of substances from each associated chamber.

As the plunger advances, the liquid and gas can be pushed distally through the device. The advancing gas can flow through small-scale geometric features such as a porous material, small hole(s), and agitation features, thus generating a cloudy mix of agitated saline and air bubbles. This cloudy mix can be produced continuously, at the same time as the substance is injected into a person. Further, the bubbles can be created close to the output of the device, such that the time for the bubbles to dissipate can be reduced. The efficient generation and advancement of the cloudy mix of agitated saline and air bubble mixture can allow lower volumes to be used.

Even further, the processes for generating the cloudy mix of agitated saline and air bubbles and injecting them into a patient can be combined into a single step: the advancement of a plunger.

Once the agitated cloudy mix is delivered to the IV of the patient, images can be captured (such as images of the heart) to indicate the presence of bubbles in various areas of the body. For example, as discussed herein, such images can potentially be used to indicate the presence of a PFO or other septal defects. Other blood carrying vessels can also be monitored, such as the arteries and veins of limbs and organs, to look for leaks elsewhere in the vascular system. Furthermore, this can be used to assist proper positioning of the catheter for other medical procedures, such as pericardiocentesis.

It will be understood that the devices described herein can be used in wide variety of situations. For example, although the device is described for use with humans, it can be used in other contexts, such as with other animals. Further, it could also be used in other situations where a cloudy mix of agitated saline and air bubbles might be need to opacify the area of interest. Additionally, the cloudy mix of agitated saline and air bubbles can potentially be generated in other ways, such as with a pressure driven mechanism, rotator driven mechanism, vibrator driven mechanism, electricity driven mechanism, magnetically driven mechanism, or any combination of such technologies.

As another example, in some embodiments it may be desirable to provide an agitated solution without air bubbles. For example, this may be desirable in pediatrics. Thus, in some embodiments, the air chamber can be removed or otherwise disabled (for example by separating a plunger for a gas chamber from a plunger for a fluid chamber). The agitated fluid (such as agitated saline) without bubbles can potentially still be visible to an ultrasound machine, such that it can be used in a similar manner.

The physical features described herein can be formed from a variety of materials. For example, the plunger 20, main body 10, and output spout 30 can be formed from polypropylene, other medical grade plastics, medical grade metals, or other materials. As discussed above, components can also be formed from rubber, neoprene, or other materials.

The various devices, methods, procedures, and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A device comprising:
   a first chamber holding a saline solution;
   a second chamber holding a gas;
   a valve separating the contents of the first and second chambers from mixing;
   an output from the device, in communication with the first and second chamber, such that the fluid and gas can flow through the output, the output comprising a taper, the taper comprising small-scale geometric features, the small-scale geometric features configured to produce gas bubbles as the saline solution and gas flow from the first and second chambers and through the output, the small-scale geometric features comprising a plurality of fins disposed along the taper; and
   a plunger configured to simultaneously force the saline solution and gas past the valve to mix with each other, through the small-scale geometric features to produce gas bubbles, and through the output,
   wherein the valve is configured to prevent mixing of the saline solution and the gas prior to movement of the plunger.

2. The device of claim 1, further comprising a screen configured to produce gas bubbles as the saline solution and gas flow from the first and second chambers and through the output.

3. The device of claim 1, further comprising one or more small holes configured to produce gas bubbles as the saline solution and gas flow from the first and second chambers and through the output.

4. The device of claim 1, wherein the small-scale geometric features are sized to produce microbubbles resulting in a cloudy mix of fluid and gas.

5. The device of claim 1, wherein the gas bubbles produced by the small-scale features have an average size between 10 and 200 microns.

6. The device of claim 1, wherein the plunger is configured to continuously force the saline solution and gas past the valve to mix with each other.

7. The device of claim 1, wherein the plunger comprises two plunger portions attached such that the two plungers can be advanced together.

8. The device of claim 7, wherein the two plunger portions can be detached such that they can be pulled-back separately to fill the first and second chambers.

9. A sterile packaging comprising the device of claim 1.

10. A device comprising:
    a first chamber holding a saline solution;
    a second chamber in communication with the first chamber, the second chamber comprising a plurality of small-scale agitation features configured to agitate the saline solution flowing to the second chamber from the first chamber by shearing the saline solution such that the saline solution becomes sufficiently cloudy for visualization using ultrasound in a medical setting without bubbles, the small-scale agitation features comprising a plurality of fins;
    a device opening in communication with the second chamber such that the agitated fluid can flow out of the device opening, the device opening comprising a taper, the plurality of fins being disposed on the taper; and
    a plunger configured to simultaneously force the saline solution from the first chamber, through the second chamber to become agitated, and further through the device opening.

11. A sterile packaging comprising the device of claim 10.

* * * * *